US010228371B2

(12) United States Patent
Baumeister et al.

(10) Patent No.: US 10,228,371 B2
(45) Date of Patent: Mar. 12, 2019

(54) LIPOSOMAL COMPOSITION COMPRISING A STEROL-MODIFIED LIPID AND A PURIFIED MYCOBACTERIAL LIPID CELL WALL COMPONENT AND ITS USE IN THE DIAGNOSIS OF TUBERCULOSIS

(71) Applicant: University of Pretoria, Pretoria (ZA)

(72) Inventors: Carl Baumeister, Menlo Park (ZA); Walter Allen Shaw, Birmingham, AL (US); Jan Adrianus Verschoor, Pretoria (ZA)

(73) Assignee: University of Pretoria, Pretoria (ZA)

( * ) Notice: Subject to any disclaimer, the term of this patent is extended or adjusted under 35 U.S.C. 154(b) by 51 days.

(21) Appl. No.: 14/406,636

(22) PCT Filed: Jun. 7, 2013

(86) PCT No.: PCT/IB2013/054686
§ 371 (c)(1),
(2) Date: Dec. 9, 2014

(87) PCT Pub. No.: WO2013/186679
PCT Pub. Date: Dec. 19, 2013

(65) Prior Publication Data
US 2015/0111219 A1 Apr. 23, 2015

(30) Foreign Application Priority Data

Jun. 11, 2012 (ZA) ................................ 2012/04273

(51) Int. Cl.
*G01N 33/569* (2006.01)
*G01N 33/92* (2006.01)
*G01N 33/543* (2006.01)
*G01N 1/38* (2006.01)

(52) U.S. Cl.
CPC ........... *G01N 33/5695* (2013.01); *G01N 1/38* (2013.01); *G01N 33/5432* (2013.01); *G01N 33/92* (2013.01); *G01N 2333/35* (2013.01); *G01N 2469/20* (2013.01); *G01N 2800/12* (2013.01)

(58) Field of Classification Search
None
See application file for complete search history.

(56) References Cited

U.S. PATENT DOCUMENTS

2016/0169905 A1* 6/2016 Verschoor .......... G01N 33/5432 435/7.1

FOREIGN PATENT DOCUMENTS

WO WO 2005/116654 A1 12/2005
WO WO 2009/064696 A1 5/2009
WO WO 2017/077493 A1 5/2017

OTHER PUBLICATIONS

International Search Report (ISR) for PCT/IB2013/054686; I.A. fd: Jun. 7, 2013, dated Sep. 17, 2013 from the European Patent Office, Rijswijk, The Netherlands.

International Preliminary Report on Patentability (IPRP), Chapter II of the Patent Cooperation Treaty for PCT/IB2013/054686; I.A. fd: Jun. 7, 2013, date of completion: Sep. 4, 2014, from the European Patent Office, Rijswijk, The Netherlands.

Huang, Z., and Szoka, F.C., "Sterol-Modified Phospholipids: Cholesterol and Phospholipid Chimeras with Improved Biomembrane Properties," Journal of the American Chemical Society, 2008, 130(46):15702-15712, American Chemical Society, United States.

Lemmer, Y., et al., "Chapter 5—Detection of Antimycolic Acid Antibodies by Liposomal Biosensors," Methods in Enzymology; Liposomes—Part F, 2009, 464:79-104, Academic Press, United States.

Thanyani, S.T., et al., "A novel application of affinity biosensor technology to detect antibodies to mycolic acid in tuberculosis patients," Journal of Immunological Methods, 2008, 332(1-2):61-72, Elsevier, The Netherlands.

Tiwari, R.P., et al., "Glycolipids of *Mycobacterium tuberculosis* Strain H37Rv Are Potential Serological Markers for Diagnosis of Active Tuberculosis," Clinical and Diagnostic Laboratory Immunology, Mar. 2005, 12(3):465-473, American Society for Microbiology, United States.

Benadie, Y et al., "Cholesteroid nature of free mycolic acids from M. tuberculosis," Chem Phys Lipids. Apr. 2008;152(2):95-103. doi: 10.1016/j.chemphyslip.2008.01.004. Epub Feb. 7, 2008.

Villeneuve, M et al., "Differential conformational behaviors of α-mycolic acids in Langmuir monolayers and computer simulations," Chem Phys Lipids. Jun. 2010;163(6):569-79. doi: 10.1016/j.chemphyslip.2010.04.010. Epub May 11, 2010.

Groenewald et al., "Differential spontaneous folding of mycolic acids from *Mycobacterium tuberculosis*," Chem Phys Lipids. May 2014;180:15-22. doi: 10.1016/j.chemphyslip.2013.12.004. Epub Dec. 18, 2013.

Beukes et al., "Structure-function relationships of the antigenicity of mycolic acids in tuberculosis patients," Chem Phys Lipids. Nov. 2010;163(8):800-8. doi: 10.1016/j.chemphyslip.2010.09.006. Epub Sep. 25, 2010.

Lemmer et al., "Mycolic acids, a promising mycobacterial ligand for targeting of nanoencapsulated drugs in tuberculosis," J Control Release. Aug. 10, 2015;211:94-104. doi: 10.1016/j.jconrel.2015.06.005. Epub Jun. 6, 2015.

* cited by examiner

*Primary Examiner* — Tracy Vivlemore
*Assistant Examiner* — Nam P Nguyen
(74) *Attorney, Agent, or Firm* — Sterne, Kessler, Goldstein & Fox P.L.L.C.

(57) ABSTRACT

A liposomal composition comprising a sterol-modified lipid and a purified mycobacterial lipid cell wall component or analog or derivative thereof is described. The composition is useful as a lipid antigen-presenting vehicle for the detection of lipid antigen specific biomarker antibodies in antibody containing biological samples in the diagnosis of active tuberculosis. The purified lipid cell wall component is typically a purified mycolic acid or a mixture of mycolic acids from a *mycobacterium* that produces mycolic acids. The sterol-modified lipid is typically a phospholipid.

13 Claims, 7 Drawing Sheets

LIPOSOMAL COMPOSITION COMPRISING A STEROL-MODIFIED LIPID AND A PURIFIED MYCOBACTERIAL LIPID CELL WALL COMPONENT AND ITS USE IN THE DIAGNOSIS OF TUBERCULOSIS

This invention relates to a liposomal composition comprising a sterol-modified lipid and a purified mycobacterial lipid cell wall component that is used as a vehicle of antigen presentation for the detection of antigen specific biomarker antibodies in the diagnosis of active tuberculosis.

To date, there is no reliable commercial detection method for the diagnosis of extrapulmonary TB, pediatric TB and HIV co-infected TB. There is also no reliable blood-based method to diagnose TB available. All commercial methods are currently based on sputum samples. The ability to accurately detect low-affinity patient anti-mycolic acids (MA) antibodies as biomarker for active tuberculosis may change all that. Such a method exists, and is called the Mycolic acid Antibodies Real-Time Inhibition test (MARTI-test) (Verschoor et al., 2005, Thanyani et al., 2008, Lemmer et al., 2009). The MARTI-test can distinguish between two low-affinity antibody systems: ubiquitously present anti-cholesterol antibodies and TB patient specific anti-MA antibodies, which cross-react. It is achieved by making use of either surface plasmon resonance (Lemmer et al., 2009), or electro-impedance biosensor technology (Mathebula et al., 2009). This invention concerns itself with improving the lipid antigen immobilisation technology to make it more amenable for practical diagnostic application on any technology platform that can support the MARTI-test.

TB Diagnostics

Tuberculosis (TB) is a bacterial disease caused by *Mycobacterium tuberculosis* that commonly infects the lungs. Currently about one-third of the World's population is infected and nearly two million deaths occur each year. It is the leading cause of death in immune compromised individuals such as HIV patients (Vassall et al., 2011). Tuberculosis is a complex disease, able to induce both a humoral and cellular immune response. Currently the gold standard for active pulmonary TB diagnosis remains clinical examination combined with examination of cultured mycobacteria from sputum (Andersen et al., 2000). This process can take at least six weeks (Van Deun et al., 2010), during which time the patient may have already infected friends and family, co-workers, passengers in communal transport and hospital staff. The smear microscopy test for Acid Fast Bacilli (AFB) is much faster and much more affordable, but of low sensitivity, typically showing up positive only in late-stage adult pulmonary TB patients, who, by this time, have suffered irreparable lung damage.

HIV Co-Infection and TB Diagnosis

GeneXpert and other nucleic acid amplification tests (NAATs) are not sensitive enough for the diagnosis of immune compromised patients such as those with HIV co-infection. With HIV co-infection, the bacilli often escape the lungs, causing the sputum to contain insufficient numbers of bacilli to be detectable with smear microscopy, mycobacterial culture or even pathogen specific NAATs (Wilson, 2005).

The WHO reported that more than 72% of patients with TB were co-infected with HIV in South Africa during 2009. South Africa also suffers from the highest prevalence of both TB and AIDS in the World (Floyd et al., 2011), thereby drastically reducing the effectiveness of the GeneXpert assay. Another complication is the antagonistic relationship between AIDS and TB that makes co-infection a death sentence within months in at least 90% of untreated patients (WHO 2011, Gandhi et al., 2006).

Diagnosis of Extra-Pulmonary TB

Extra-pulmonary TB occurs from infection of lymph nodes, pleural or meningeal tissues, central nervous system, bone and or joint, genitourinary organs, abdominal cavity, skin and other disseminated sites (Steingart et al., 2011). Diagnosis of extra-pulmonary TB poses several challenges that have not yet been solved with a specific diagnostic method. This forces clinicians to prescribe long term treatment for high-risk patients solely on an empirical basis (Rao, 2007), burdening such patients with therapeutic side-effects that could have been avoided by accurate diagnosis. The need for a functional serological extra-pulmonary TB diagnostic is therefore well defined.

Diagnosis of Paediatric TB

Tuberculosis diagnosis in children appears more complicated than in adult patients. This is due to low bacillary load that is usually obtained in sputum samples. A recent investigation into the GeneXpert system for its ability to detect paediatric TB was done in 2011. Results indicated a 98.8% specificity but sensitivity as low as 27.8% for smear negative children aged 15 and younger (Nicol et al., 2011). This implies that paediatric TB remains difficult to diagnose despite development of modern diagnostics.

Immunoassays

The underlying principle for antibody immunoassays is the detection of binding of an antibody to an antigen. Immunoassays exploit the fact that in response to foreign organisms such as bacteria and viruses, the immune system will produce antibodies with high specificity to an almost infinite number of antigens. These antibodies are produced with the aim of marking the target cell for destruction. If one could obtain purified antigen, the antibodies specific to the antigen can be detected in an immunoassay.

Generally used formats for immunoassays are the mixing of antigens and antibodies, one of which is either labelled or attached to a surface. If the antibody recognizes the antigen, binding will occur. Experimentally the event is registered by means of a colour change, fluorescence, radiation emission, agglutination or precipitation. A major milestone in diagnostic immunoassays called ELISA was invented by Engvall & Perlmann (Engvall & Perlmann, 1971). A massive shift towards immunoassays in disease diagnostics ensued, due to much improved levels of sensitivity and specificity (Zhou et al., 2011). To date, however, the WHO through their evaluation of tests currently being sold on the market (Steingart et al., 2011) could not find a single reliable TB diagnostic lateral flow immunoassay. The authors report that these tests continue to produce inconsistent and imprecise estimates of sensitivity and specificity. Biomarker antibodies in serum range from IgM during the early stages of infection to IgG in the latter stages of infection. This produces a challenge for the design of a serodiagnostic device, because of the difference in binding kinetics and thermodynamics of IgG and IgM.

Biomarker Serum Antibodies as Diagnostic Indicators

Many biomarker antibodies from serum have been used for diagnostic immunoassay purposes, eg. for diagnosis of multiple sclerosis and Crohn's disease (Dotan et al., 2006), HIV diagnosis (Kaufman & Ross, 2010) systemic lupus erythromatosis (Liu et al., 2005), Hepatitis B (He et al., 2003b), Hepatitis C (Okochi et al., 1991), and TB (He et al., 2002).

The discovery of biomarkers is important for disease diagnosis (Lescuyer et al., 2007). A good biomarker should be highly specific to a disease, easily detected and able to differentiate affected from non-affected patients. The advantage of detecting biomarker antibodies, rather than traces of the infective organism, is that antibodies are freely available in serum, whereas microorganisms can evade detection by hiding in cells and tissues.

The Challenge of Low-Affinity Antibodies

The early immune response will generate low-affinity IgM antibodies that display high binding avidity due to their polymeric structure (Liang et al., 2007). The detection of these primary antibodies are important in immunoassays for early diagnosis. ELISA is an inexpensive and rapid method for detection of antibodies that makes use of a wash step to remove unbound antibodies, but that may also remove the bound low-affinity antibodies, thereby giving rise to a signal that is biased towards high-affinity antibodies (Liang et al., 2007). This makes low-affinity antibodies undetectable. The factors that contribute to the difficulty of detection of low-affinity antibodies include washing, buffer constituents, and incubation times (Mire-Sluis et al., 2004). Successful detection of low affinity anti-mycolic acid antibodies for TB diagnosis was reported by Lemmer et al., 2009, with evanescent field biosensing. This technology obviates the need for separation of bound and free antibodies by washing and requires no signal amplification steps after antibody-antigen exposure.

The Mycolic Acid Antibodies Real-Time Inhibition (MARTI) Assay

Mycolic acids are accommodated in phosphatidylcholine liposomes that allow the presentation of the mycolic motif on the aqueous outer surface for the MARTI diagnostic procedure. Details of the procedure can be found in the Marti patent (Verschoor et al., 2005).

Perhaps the greatest advantage of the MARTI assay is the ability to detect low-affinity antibodies. In fact, MARTI using SPR is most probably the first assay to detect low-affinity antibodies in TB diagnostics. The use of biosensor based technology for TB diagnosis has been demonstrated well in wave guide (Thanyani et al., 2008) and SPR (Lemmer et al., 2009) evanescent field biosensors.

Limitations of SPR in the MARTI Assay

The limitations of the MARTI assay include liposome antigen carriers with limited stability which contribute to a large number of failed runs. Thus, optimisation of the surface chemistry for MA antigen coating of sensor surfaces is of utmost importance to the feasibility of the MARTI assay as a diagnostic test.

Liposomes

Liposomes were formally described by Bangham in 1961 (Sattler, 2010), evident through electron microscopy and negative staining. Lemmer et al. (2009) described their application as lipid antigen carrier and presenter in the MARTI test for TB diagnosis. The addition of cholesterol into liposomes causes an increase in membrane stability by increasing the crystal packing parameter and decreasing membrane fluidity. Cholesterol also reduces the hydrophile lipophile balance (HLB) that is involved in membrane curvature. A reduced HLB will result in membranes with less curved surfaces, i.e. larger sizes.

The Hydrophile Lipophile Balance (HLB) is a numerical scale from 40 to 1 indicating whether a surfactant for a system will allow formation of an O/W or W/O emulsion (See FIG. 1). The crystal packing parameter (CPP) is defined as $v/(l.a_0)$ where (v=partial molar volume of surfactant hydrocarbon chain=0.027 (#C's without Me group+#Me groups). l=length surfactant hydrocarbon chain=0.15+ 0.127#C's (or 70-80% of fully extended length) and $a_0$=optimal head group area. Where the CPP is small, liposomes will have a small size and when the CPP approximates a value of 1 the largest liposomes are likely to form in an aqueous environment. This is true for the case of both cholesterol and mycolic acids containing liposomes.

Characterisation of liposomes is based on methods including initial structure, size, stability, zeta potential and polydispersity index and whether they form a micro-emulsion (as O/W or W/O). As liposomes have been widely investigated for their ability to deliver drugs in vivo, many studies have been undertaken to address problems that may arise with changes in pH, temperature and ionic strength on liposome stability, aggregation and fusion. It is therefore important to measure and define physical stability of liposomes for each particular application, including that of biosensor diagnostics. Physical stability can be investigated with photon correlation spectroscopy—measured by a so-called Zeta-sizer device that measures particle size, polydispersity and zeta potential (Grohmann et al., 1998).

The zeta potential of a particle is defined as the overall charge that it acquires in a specific medium (Zetasizer Nano application note MRK575-01). Zeta potential relates to liposome stability by preventing fusion through charge repulsion (Akashi et al., 1998). The theory by which this occurs is called the Deryaguin-Landau-Verwey-Overbeek (DLVO) theory, whereby an electrostatic force provided by the Van der Waals interaction creates separation. It has been realized that zeta potential is an indicator of colloid (liposome) stability (Li & Tian, 2002). Most particles dispersed within an aqueous system will acquire a surface charge either by surface group ionization, or adsorption of charged species. These surface charges then modify the distribution of the surrounding ions, resulting in a layer around the particle that is different from that of the bulk solution. If the particle moves under Brownian motion (Uhlenbeck & Ornstein, 1930), this layer will move as part of the particle. The zeta potential is the potential at the point in this layer where it moves past the bulk solution. This is usually called the slipping plane. The charge at this plane is very sensitive to the concentration and type of ions in solution (Malvern, 2009). This technique is based on laser Doppler velocimetry (Zetasizer Nano application note MRK575-01).

Liposomes/particle size can be measured by dynamic light scattering (DLS). It measures the time-dependent fluctuations in the intensity of scattered light due to Brownian motions of the particles. Analysis of the intensity fluctuations enables determination of diffusion coefficients that can then be converted into a size distribution (Zetasizer Nano application note MRK575-01). This size distribution is a measure of a diverse size range, called the polydispersity. The polydispersity is best visualised as a Gaussian distribution. This is because, in a liposomal system, a sample population of liposomes will not be a uniform size, but is better represented by a size distribution.

Conventionally, the MARTI assay has used phosphatidylcholine (PC) to form the basic structure of the liposome carrier for mycolic acid antigens. Proof of this principle for TB diagnosis has been provided by Thanyani et al. (2008), who also showed that the liposomes were of limited stability, causing a high level of variance in the biosensor results. The instability arises from changes in liposome size over time. This increase in the average size of the liposomes gives them a greater electrostatic energy (Winterhalter & Lasic, 1993). The increase in electrostatic energy results in an increased zeta potential, a known marker for liposome stability (Li & Tian, 2002). In literature the addition of cholesterol has been proven to stabilise membranes (Connor et al., 1984). The sterol structure in cholesterol is a rigid plane, formed by three cyclohexane rings and a single cyclopentane, which reduces phospholipid motility and vibrational energy of the hydrocarbon chains. The addition of cholesterol to the liposome system should improve liposome stabilization, but in the MARTI application this is not feasible, as cholesterol is a reactive component in the detection of anti-MA antibodies in patient sera. Benadie et al. (2008) namely demonstrated a cross-reactivity of patient serum antibodies with mycolic acids and cholesterol. Alternative lipids had to be investigated for liposome stabilisation in the MARTI-test.

This invention provides a stable lipid antigen carrier and presentation particle that allows better antibody recognition of mycolic acid antigens by TB patient antibodies in the MARTI test for extra-pulmonary, pediatric and or HIV co-infected adult TB diagnosis. It is achieved by the incorporation of a specific sterol modified lipid into phosphatidylcholine liposomes.

SUMMARY OF THE INVENTION

The invention provides a liposomal composition comprising a sterol-modified lipid and a purified mycobacterial lipid cell wall component or analogue or derivative thereof. In particular, the invention provides a lipid antigen-presenting liposomal composition for the detection of lipid antigen specific biomarker antibodies in antibody containing biological samples, the composition including liposomes comprising a sterol-modified lipid and a purified mycobacterial lipid cell wall component or analogue or derivative thereof.

The sterol-modified lipid may be a sterol-modified phospholipid. More particularly, the sterol-modified lipid may be a sterol-modified phosphatidylcholine lipid. Still more particularly, it may be a sterol-modified glycerophospholipid.

The sterol may be linked to the glycerol moiety of the sterol-modified glycerophospholipid by an ester, carbonate, carbamate or ether link. The sterol-modified lipid may have one or more $C_{14}$-$C_{18}$ acyl chains. The sterol may be cholesterol. The sterol-modified lipid may, in particular, be 1-palmitoyl-2-cholesterylcarbonoyl-sn-glycero-3-phosphocholine.

The composition may contain about 20-55 mol percent of liposomes comprising the sterol-modified lipid and the purified mycobacterial lipid cell wall component and about 45-80 mol percent of liposomes comprising phosphatidylcholine. The composition may preferably contain about 35-45 mol percent of liposomes comprising the sterol-modified lipid and the purified mycobacterial lipid cell wall component and about 55-75 mol percent of liposomes comprising phosphatidylcholine. In an embodiment of the invention it may for example contain about 30 mol percent of liposomes comprising the sterol-modified lipid and the purified mycobacterial lipid cell wall component and about 70 mol percent of liposomes comprising phosphatidylcholine.

In an embodiment of the invention, there is provided a lipid antigen-presenting composition for the detection of lipid antigen specific biomarker antibodies in antibody containing biological samples, the composition comprising a sterol-modified lipid, a purified mycobacterial lipid cell wall component and phosphatidylcholine.

The composition may comprise 20-50 mol percent of the sterol-modified lipid and the purified mycobacterial lipid cell wall component and 45-80 mol percent of the phosphatidylcholine. It may, for example, comprise 30 mol percent of the sterol-modified lipid, 10 mol percent of the purified mycobacterial lipid cell wall component and 60 mol percent of the phosphatidylcholine.

The purified mycobacterial lipid cell wall component may be derived from mycobacteria selected from virulent and pathogenic mycobacteria. In particular, the purified mycobacterial lipid cell wall component or analogue or derivative thereof may be derived from *Mycobacterium tuberculosis*. The purified mycobacterial lipid cell wall component may be in a form selected from homogenous and heterogeneous compound mixtures.

The liposomal composition may primarily be composed of phosphatidylcholine.

The sterol-modified lipid component may accommodate a sterol moiety in covalent linkage, including ester, carbonate, carbamate and ether linkages.

The sterol-modified lipid component may be a modified glycerophosphatidylcholine with acyl chain lengths of $C_{14}$-$C_{18}$.

In a preferred embodiment of the invention the mycolic acid antigen is first mixed with a phospholipid composition of which the sterol-modified phospholipid comprises about 30 mol %, to produce liposomes having mycolic acid antigen integrated into the liposome phospholipid surface layer. Typically, production of the liposomal composition will involve sonication of the phospholipid-antigen mixture.

According to another aspect of the invention there is provided a diagnostic method, in which the liposomal composition described above provides a stable vehicle of mycobacterial lipid cell wall antigen presentation for the detection of antigen specific biomarker antibodies in the diagnosis of active tuberculosis.

The diagnostic method may be a modified Mycolic acid Antibodies Real-Time Inhibition (MARTI) test that was originally described in a patent by Verschoor J. A. et al 2005.

The diagnostic method may be performed on biosensors, such as surface plasmon resonance or electrochemical impedance biosensors.

According to a second aspect of the invention, there is provided a method of preparing a lipid antigen-presenting liposomal composition for the detection of lipid antigen specific biomarker antibodies in antibody containing biological samples, the method including the steps of combining a sterol-modified lipid and a purified mycobacterial lipid cell wall component or analogue or derivative thereof to produce liposomes having mycolic acid antigen integrated into the liposome surface layer.

The lipid antigen-presenting liposomal composition may be as hereinbefore described.

According to another aspect of the invention, there is provided a method of detecting antigen specific biomarker antibodies for the diagnosis of active tuberculosis, the method including the steps of providing a lipid antigen-presenting liposomal composition comprising liposomes comprising a sterol-modified lipid and a purified mycobacterial lipid cell wall component or analogue or derivative thereof as hereinbefore described;

immobilizing the liposomes to produce immobilized mycolic acid antigens comprising the purified mycobacterial lipid cell wall component or analogue or derivative thereof;

obtaining a first, a second and a third sample from a human or animal suspected of having active tuberculosis, wherein each sample may contain antibodies to the antigen, the first sample having a lower concentration by dilution than the second and third samples;

exposing part of the first sample to the immobilized mycolic acid antigens in a test vessel;

exposing part of the first sample to the immobilized mycolic acid antigens in a control vessel;

exposing the second sample to the lipid antigen-presenting liposomal composition provided in the first step;

exposing the third sample to liposomes not containing mycolic acid antigen;

adding the second sample, after exposure to the mycolic acid antigen-containing liposomal composition provided in the first step, to the test vessel;

adding the third sample, after exposure to the liposomes not containing mycolic acid, to the control vessel;

detecting binding of antibodies to the mycolic acid antigen in both the test and control vessels in real time; and comparing the degree or extent of binding between the test and the control vessels, the weaker binding in the test vessel being an indicator of the presence of antibodies to the mycolic acid antigen in the sample that indicates active tuberculosis in the human or animal from which the sample originated.

Immobilizing the liposomes to produce immobilized mycolic acid antigens comprising the purified mycobacterial lipid cell wall component may be carried out on an activated surface. The activated surface may be a hydrophilic, underivitised biosensor cuvette surface.

The method may include the use of a biosensor selected from surface plasmon resonance biosensors and electro-impedance biosensors. The electro-impedance biosensor may include screen printed electrodes. In particular, the method may be carried out using the modified mycolic acid antibodies real-time inhibition (MARTI) procedure.

The mycolic acid antigen-containing liposomal composition in the test and control vessels to which the first preparation is exposed may be immobilized mycolic acid antigen. Methods of immobilization may include methods known to one skilled in the art. Preferably the mycolic acid antigen-containing liposomal composition may be immobilized on an activated surface. In a preferred embodiment of the invention the activated surface may be a hydrophilic, underivitised biosensor surface.

The first, second and third preparation of the sample from human or animal origin will preferably be derived from an original sample by dividing the original sample into at least the first, second and third preparations before dilution.

Exposure of the first preparation of human or animal origin to mycolic acid antigen in the test and control vessels may include exposing the sample preparations of human or animal origin to a surface prepared by the prior coating of the surface with mycolic acid antigen and a suitable blocking reagent. Typically such a blocking reagent is saponin or casein.

The detection of binding of antibodies and/or other material to the mycolic acid antigen may be carried out in an automated device.

The detection of the binding of the antibodies and/or other material to the mycolic acid antigen may be carried out in real time.

The invention is now illustrated, by way of example, with reference to the following non-limiting Example and the accompanying Figures in which FIG. 1 shows the relationship between the Hydrophile Lipophile Balance (HLB) and the Crystal Packing Parameter (CPP) relating to the curvature of a phospholipid membrane; as the HLB decreases from left to right, the CPP value increases; the spheres represent the hydrophilic heads and the cylindrical shapes represent the hydrophobic tails of the phospholipids; reference numeral 1 shows tightly packed phospholipids likely to form small liposomes in aqueous environment, reference numeral 2 shows intermediate size liposomes with large hydrophobic portions likely to form large liposomes in aqueous environments and reference numeral 3 shows the orientation of lipophilic portions in a water in oil emulsion; standard PC will be found on the left side of the drawing, forming small liposomes; the SML compounds containing a cholesterol moiety will be represented more to the middle of the drawing where an increase in the size of the liposomes is observed; to the extreme right of the drawing, liposomes will disintegrate and form insoluble lipid bodies in an aqueous environment.

Figure 6:
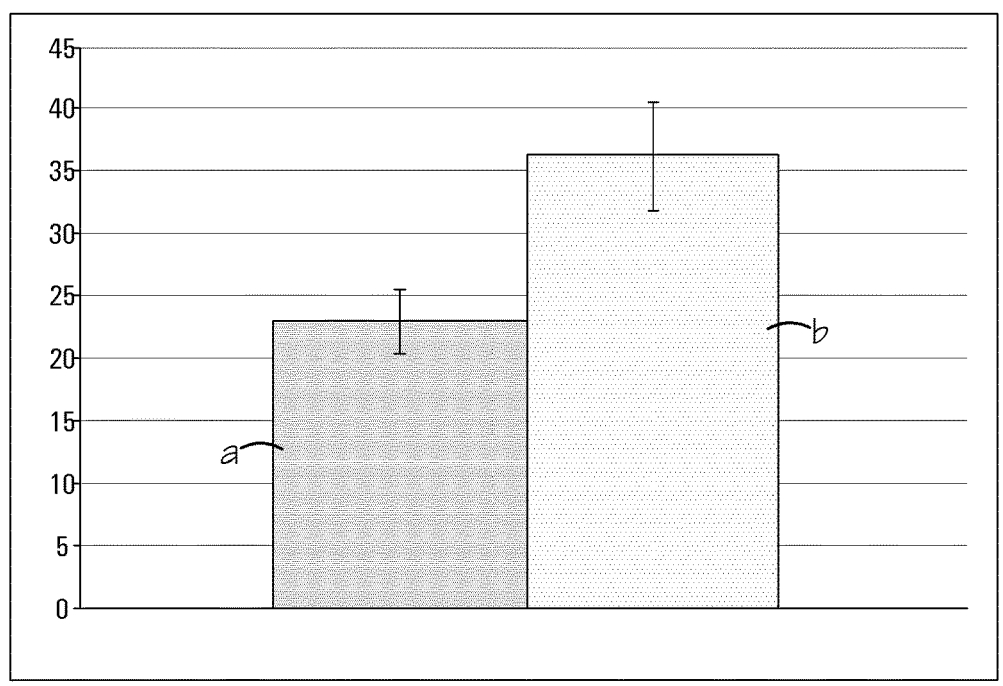
Figure 7:
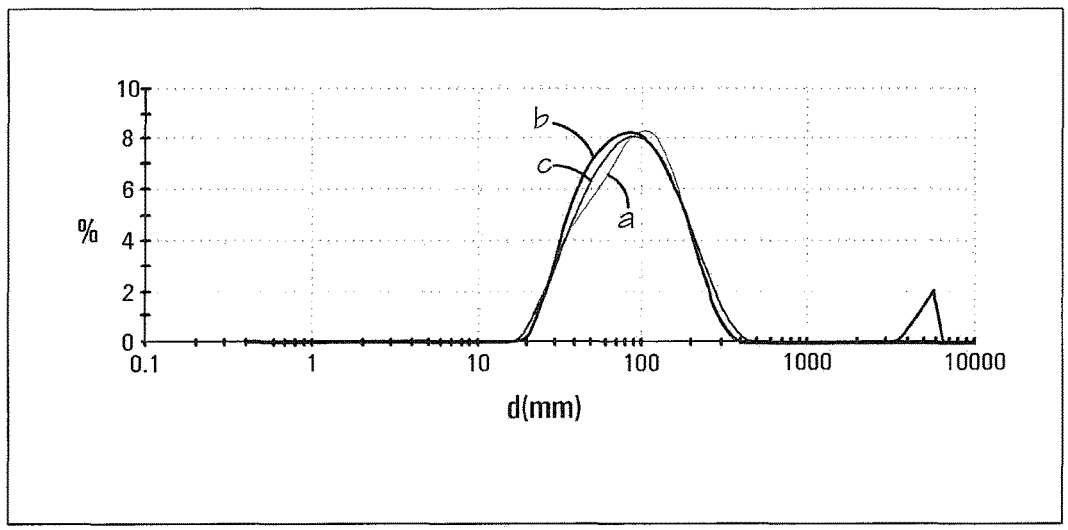
Figure 8:
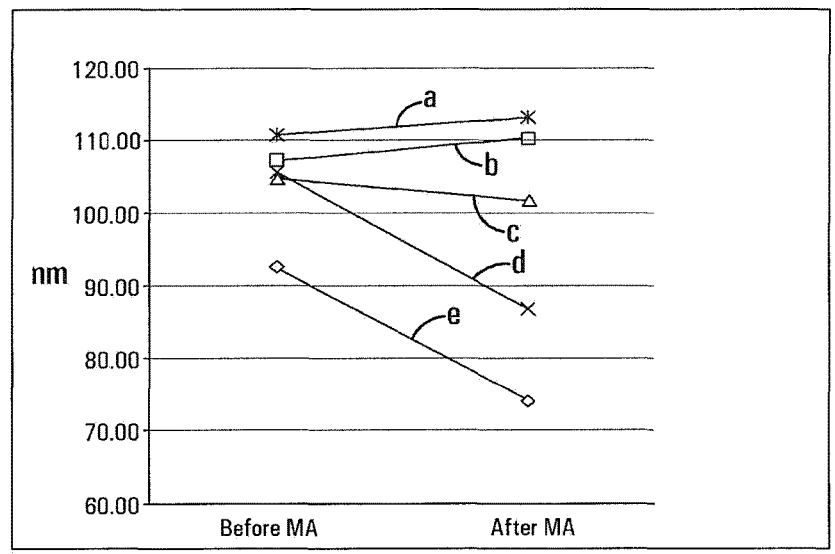
Figure 9:
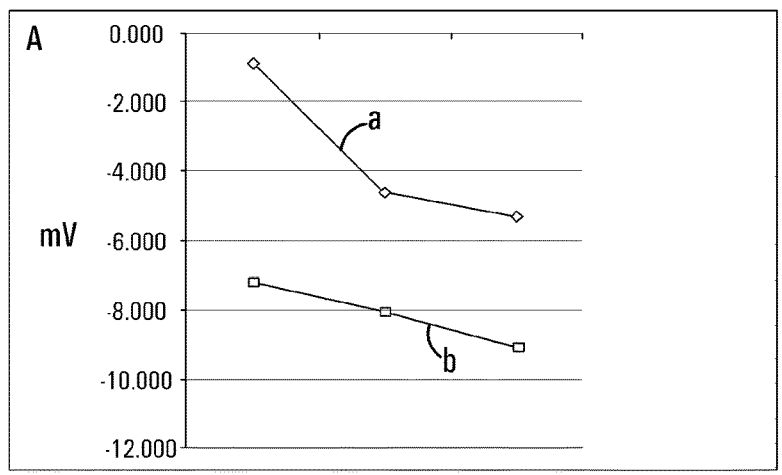
Figure 9:
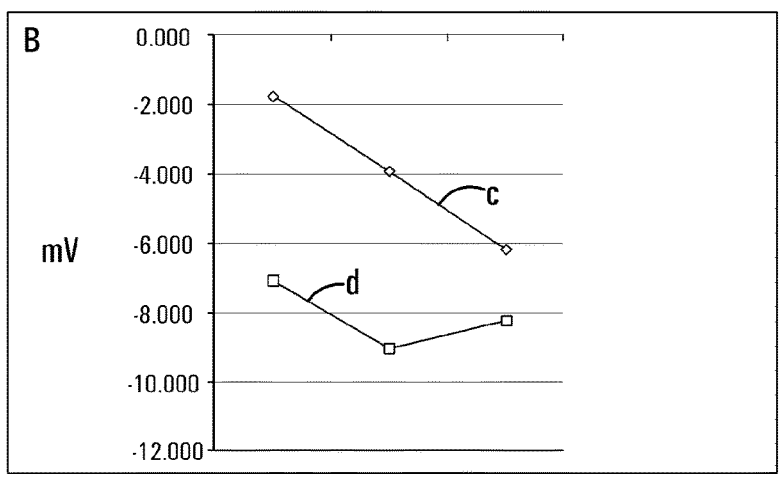
Figure 9:
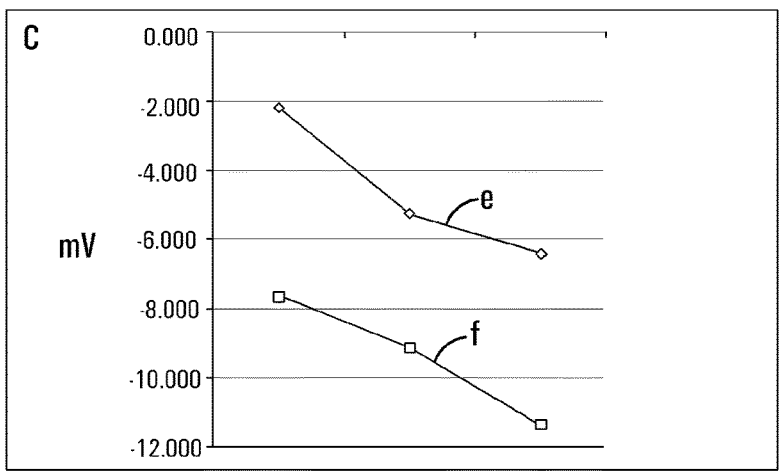

FIG. 6 shows a comparison between liposomes and their ability to distinguish between TB-positive and TB-negative patient sera in a MARTI SPR test, (a) NormPC, (b) PChcPC; values represent the mean percentage gradient difference between pooled TB-positive and TB-negative sera; error bars represent the standard error of the mean, n=6, statistically significant for P>0.05 using student's t-test, assuming unequal variances where $t_{stat}$ 2.68>$t_{crit}$ 2.31 for 8 degrees of freedom;

FIG. 7 shows a size distribution plot of normal PC liposomes against light intensity for a single time point using a Zetasizer;

FIG. 8 shows the change in size of SML-liposomes compared to NormPC-liposomes before and after inclusion of mycolic acids, (a) NormPC, (b) PChemsPC, (c) OChemsPC, (d) PChcPC and (d) DChemsPC; results were reproducible when repeated one year later; and FIG. 9 shows changes in zeta potential (mV) over time at intervals 1, 24, and 120 hours of the two most relevant SMLs; graph A (a) NormPC and (b) NormPC with MA; graph B (c) PChemsPC (d) PChemsPC with MA and graph C (e) PChcPC and (f) PChcPC with MA; standard deviation was negligible, n=90 for each value.

EXAMPLE

Reagents and Buffers.

Reagents were of at least 99% purity from either Sigma or Merck.

20× PBS:

The following compounds were weighed, 160 g NaCl, 4 g KCl, 4 g $KH_2PO_4$, 21 g $Na_2HPO_4$ and then dissolved overnight in 600 ml double distilled de-ionized (ddd) H$_2$O. The solution was then made up to 1 liter with ddd H$_2$O.

1× PBS/AE:

To make the buffer, 0.3802 g Na$_2$EDTA, 0.250 g NaN$_3$ and 50 ml 20× PBS were mixed with 900 ml dddH$_2$O, and adjusted to pH 7.44 with 1 M acetic acid. The solution was then made up to 1 liter with ddd H$_2$O and filtered through 0.2 μm cellulose acetate filters (Sartorius Stedim biotech, Germany).

Sterol-Modified Phospholipids (SML)

Figure 1:
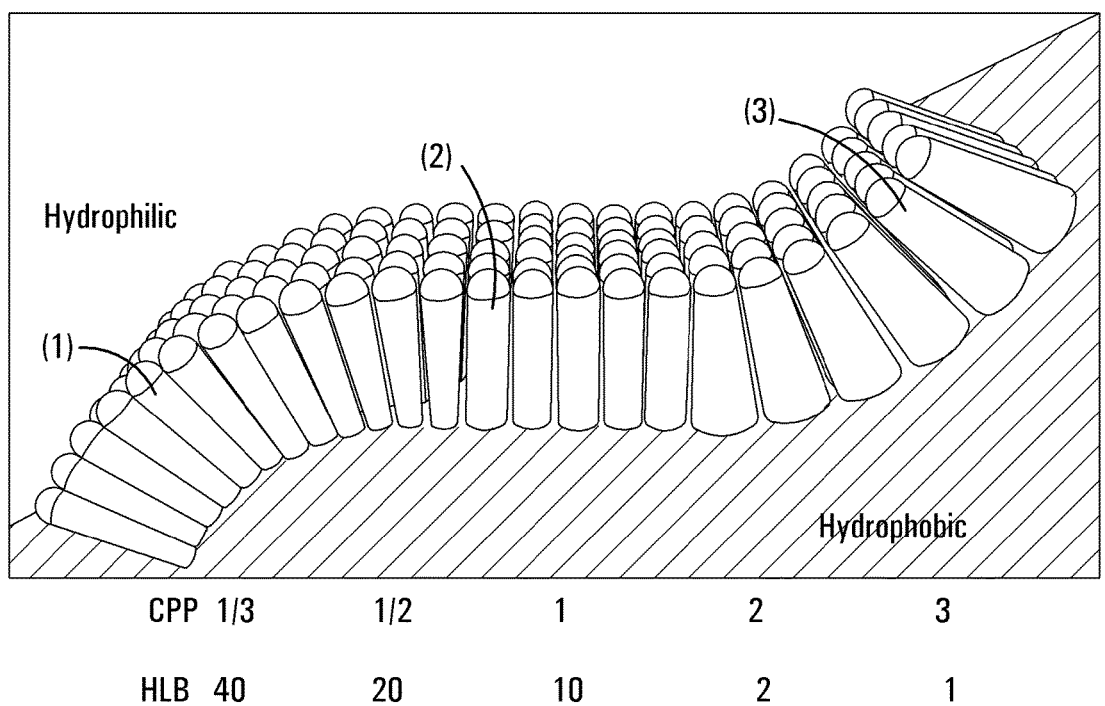
Figure 2:
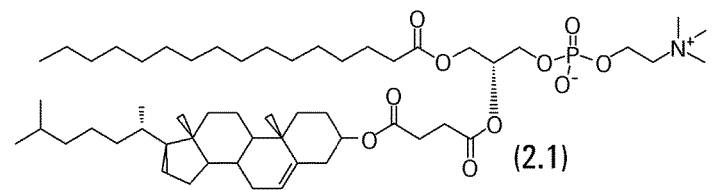
FIG. 2 shows the structures of the four sterol-modified phospholipids used in the MARTI-assay, PChemsPC (2.1), OChemsPC (2.2), PChcPC (2.3) and DChemsPC (2.4)
Figure 2:
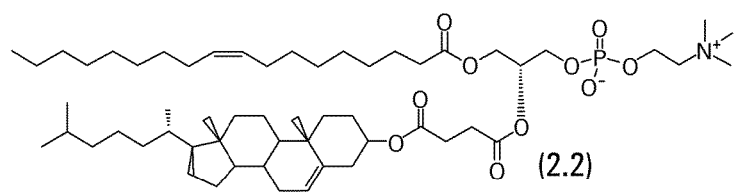
Figure 2:
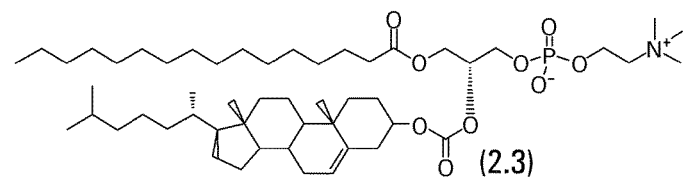
Figure 2:
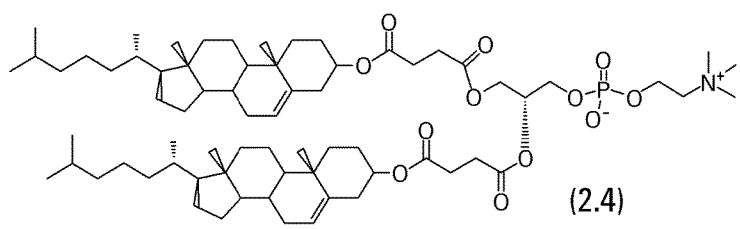

The SML compounds shown in FIG. 2 were contributed by Dr. Walt Shaw of Avanti Polar Lipids Inc., AL, USA.

PChemsPC—1-palmitoyl-2-cholesterylhemisuccinoyl-sn-glycero-3-phosphocholine

OChemsPC, 1-oleoyl-2-cholesterylhemisuccinoyl-sn-glycero-3-phosphocholine

PChcPC—1-palmitoyl-2-cholesterylcarbonoyl-sn-glycero-3-phosphocholine

DChemsPC—1,2-dicholesterylhemisuccinoyl-sn-glycero-3-phosphocholine

Saline Solution:

NaCl (0.9 g) in 100 ml ddd H$_2$O

ODT Solution (0.1 M): (for coating of gold discs)

Octadecane thiol (ODT, Sigma, 0.14329 g) was dissolved in 50 ml absolute ethanol, sonicated in a bath sonifier (Branson model 42) for 30 minutes or until dissolved. The sample was split in two. A gold coated sensor disc, (Eco Chemie, the Netherlands) was placed upright in each of the two ODT containing 50 ml centrifuge tubes overnight.

Methods

Liposome Preparation Using Sterol-Modified Lipids (SML):

Small cardboard boxes were packed with brown glass vials, covered with foil and then autoclaved. After this, the boxes were placed in a 110° C. oven until dry (overnight). The dried vial box was then stored in a desiccator overnight to cool and remain dry. PC (phosphatidylcholine) (33 mg/ml) and SML-PC (Sterol-modified PC, Avanti Polar Lipids, AL, USA) (16.5 mg/ml) chloroform solution: in an autoclaved, dried, brown glass vial, 0.012 g PC was weighed using an analytical balance. In the same vial 0.006 g of each SML class of interest was weighed. Analytical grade chloroform (360 μl) was added to the PC-SML mixture, followed by vortexing and heating to 85° C. to dissolve it completely. The vial was returned to the 4° C. fridge for 10 min to cool the chloroform.

Stock Mycolic Acid Solution (1 mg/ml):

To re-constitute previously aliquotted mycolic acid, a 1 mg sample was dissolved in 180 μl Analytical grade chloroform, followed by vortexing at 85° C. until dissolved. Cooled PC-SML-solvent solution (180 μl) was pipetted into the mycolic acids containing vial. This was then vortexed and heated to 85° C. until mixed to homogeneity. The solvents were then evaporated by heating, and nitrogen displacement for 5-10 min using a Reacti-Vap®, (Thermo Scientific, Newington, USA). Saline (0.9%, 2 ml) was added to both MA-SML-PC and SML-PC solutions. To induce liposome formation, the liposomal samples were vortexed for 20 s, heated to 85° C. for 5 min and then re-vortexed for 20 s. This process was repeated four times. The tip sonicator (Tomy UD-201 Ultrasonic disruptor, Tokyo, Japan) was cleaned by sonicating in solutions, acetone, CHCl$_3$ and ddd H$_2$O for 30 s each. All solutions were replaced every three days of operation. The PC-SML and the PC-SML-MA liposomes were sonicated at an output of 20% on a 50% duty cycle for 5 min.

The sample chamber of a freeze-dryer (Virtis, SP Industries, Gardiner, N.Y., USA) was wiped down with absolute EtOH and left to dry. The sonicated PC-SML and MA-SML-PC solutions were aliquotted separately into 200 μl samples, covered with two layers of lab paper and wrapped in elastic bands. Aliquots were frozen at −70° C. for 30 min. Samples were then freeze-dried overnight in a vacuum of 200 mtorr or less. Lab paper and elastic bands were removed, vials were capped and stored at −70° C. until use.

To reconstitute liposomes for daily use 2 ml 1× PBS/AE buffer was added to both freeze-dried samples (PC/PC-SML and PC/PC-SML-MA), vortexed and heated 85° C. for 20 minutes, with vortexing every five minutes. The sonicator tip was cleaned (30 s Chloroform, 30 s Acetone, 30 s ddd H$_2$O). The PC/PC-SML vial was sonicated first at an output of 20% with a duty cycle of 50% for five minutes, followed by the PC-MA vial. The sonicator was cleaned as before and after each use.

Liposomes were allowed to stand for at least 30 minutes before use.

Determination of liposome stability using the Zetasizer.

After reconstitution and sonication, samples were transported to the Materials Science and Manufacturing Division of the Council for Scientific Industrial Research (CSIR) in Pretoria, where the liposomes were characterised using a Zetasizer Nano ZS (Malvern Instruments, U.K.).

Clear disposable cells and plugs were washed with absolute ethanol three times, then three times with 18 MΩ ddd H$_2$O and each cell shaken dry. A 900 μl sample was then pipetted into one of the openings of the cell and the plugs were inserted. The cell was wiped with a paper towel and inserted into the Zetasizer. Sample size was measured first with the following settings: Manual, material set to phospholipids, using Mark-Houwink equation setting, dispersant=ICN PBS Tablets, Refractive Index (RI)=1.330, viscosity=0.8882 Pa·s, dispersity dielectric constant=79.0. Measurement was set to equilibrate the sample for 60 seconds. Three measurements of 11 runs each were recorded to give a total of 33 measurements per sample. Zeta potential measurements were done using the Smoluchowski equation (done by the device) using 30 measurements each in triplicate to give a total of 90 values, which were then averaged to calculate the Zeta potential.

SPR Based MARTI

The methodology pertaining to the SPR based MARTI is described in Lemmer et al. (2009). The same method was used here, except for the replacement of 30% of the PC with 30% w/w sterol-modified lipids, in both the PC liposomes and the PC-MA liposomes. This was done for all four compounds to investigate each compound's effect, using previously determined TB-negative sera ASPA004, JS09 and TB-positive sera ASPA019, BM12. Biosensor experiments were performed in triplicate unless otherwise stated. The program sequence used on the ESPRIT biosensor was a modified version of that published by Thanyani et al. (2008). The same sequence was used with a few modifications to prevent bubbles and allow simpler automation.

Results and Discussion

Sterol-modified Lipids Compared to Phosphatidylcholine as Liposomal Antigen Carriers in MARTI Assay The MARTI test for TB diagnosis is at the stage of development where proof of principle has been achieved. It is now to be developed into a design that will be suitable for validation. One challenge appeared to be the relative instability of the antigen carrying liposomes that are used for MA antigen immobilization. A typical MARTI profile is originally described by Thanyani et al. (2008).

For SPR measurement in MARTI, there should be little to no difference between the red and the green line during the high dilution serum exposure step—between 3100 and 3600 seconds, because the cuvette contents are identical during this phase. Abortive runs due to unstable liposomes manifest often during this and the next stage, probably due to the increasing burden of antibody binding to the liposomes. The high dilution step is a quality assurance step for MARTI, ensuring that the measurement of antibody binding activity in the two cells of the cuvette is comparable. This rule is complied with in both FIGS. 3 and 4, giving legitimacy to the reproducible outcomes of a reduced, or similar gradient in channel 1 compared to channel 2 at the second serum exposure, with differentially treated TB-positive patient serum and TB-negative patient serum respectively.

Figure 3A:
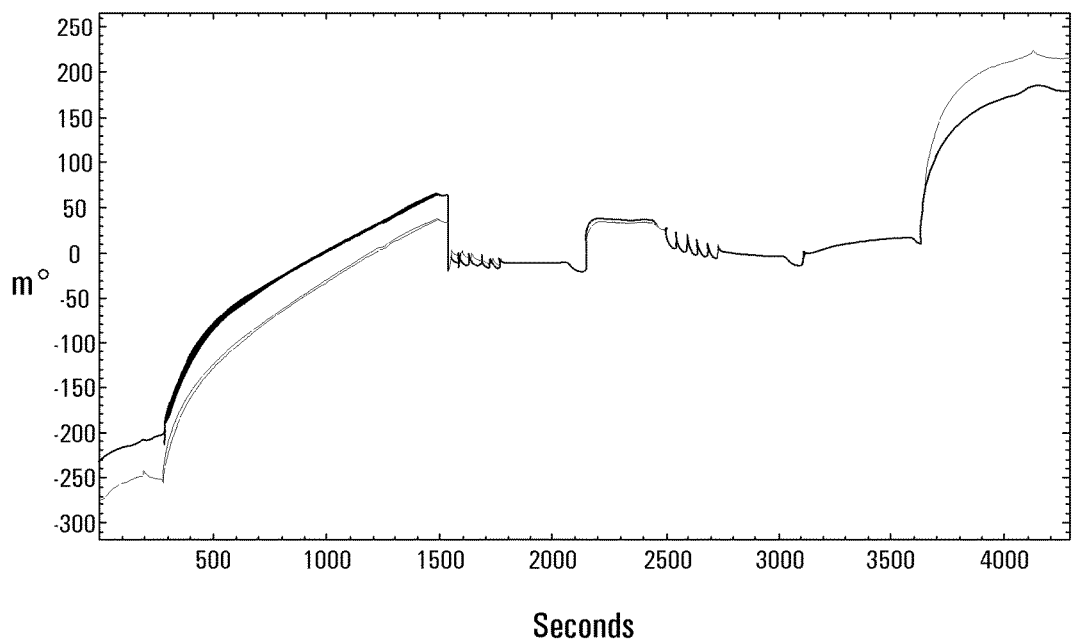
FIG. 3 shows a MARTI plot of TB-positive patient serum using PChcPC SML, confirming TB-positive status of the sample by the large difference in gradient between channel 1 and 2 during the inhibition step; SML compounds were tested as 33% (m/m) compositions with PChcPC to the PC and PC-MA liposomes; the different initial gradients during the inhibition step confirm the TB-positive status.
Figure 3B:
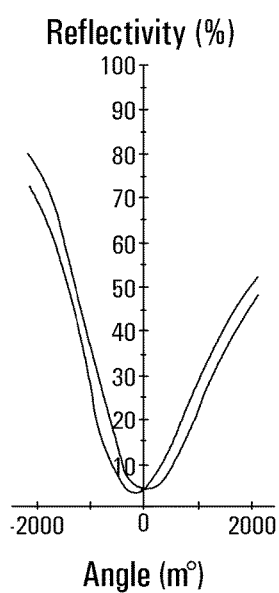
Figure 3C:
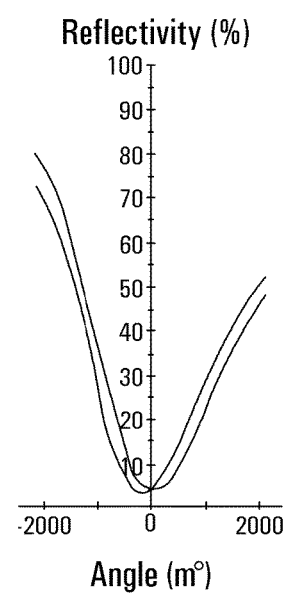
Figure 4A:
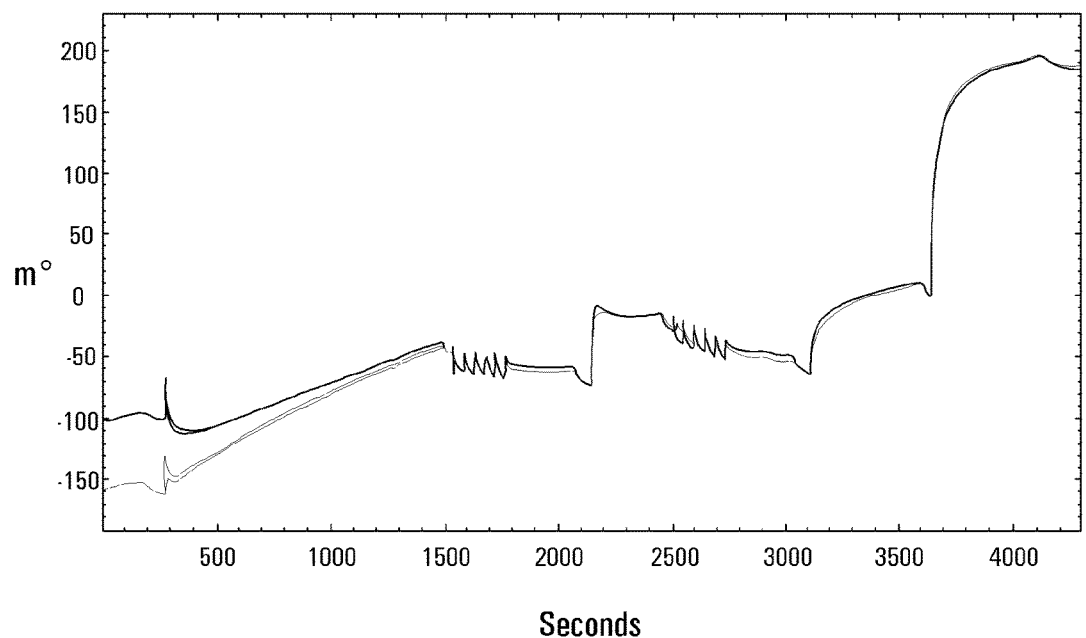
FIG. 4 shows a MARTI plot of TB-negative patient serum using PChcPC SML, confirming TB-negative status of the sample by almost no difference in gradient between channel 1 and 2 during the inhibition step; SML compounds were tested as 33% (m/m) compositions with PChcPC to the PC and PC-MA liposomes; the almost identical initial gradient during the inhibition step confirms the TB-negative status.
Figure 4B:
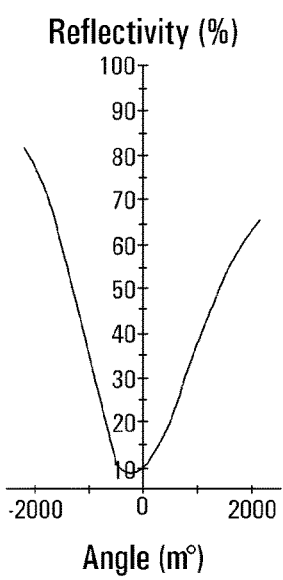
Figure 4C:
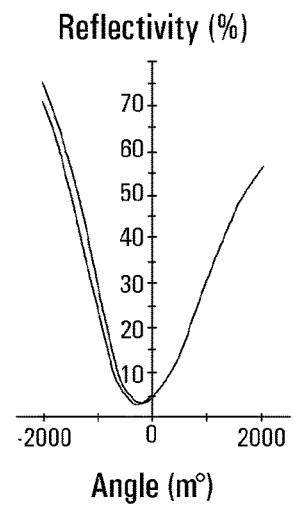
Figure 5:
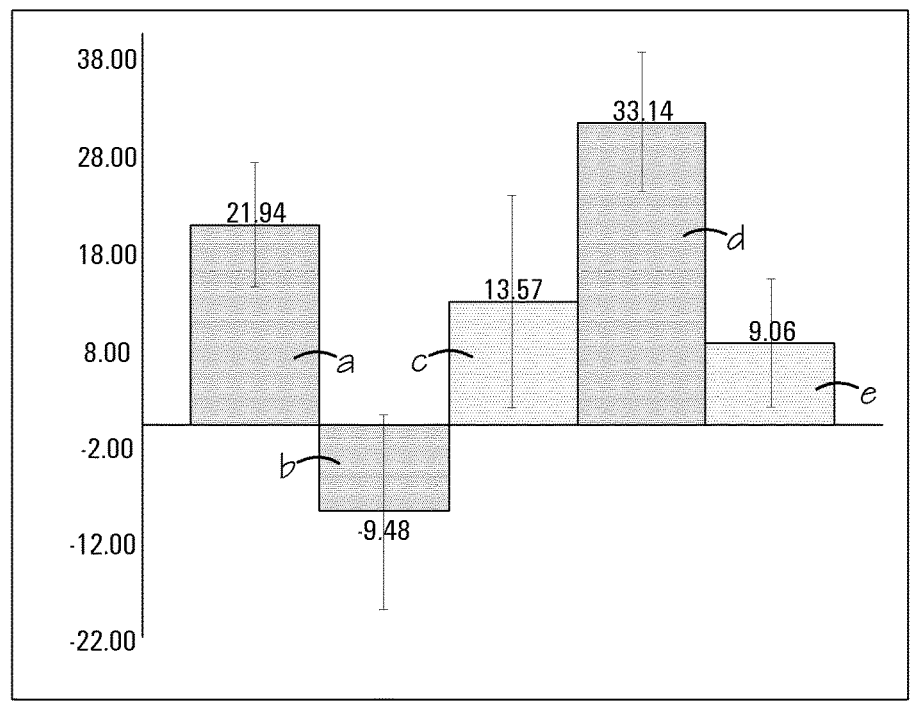
FIG. 5 shows a comparison of liposomes and their ability to distinguish between TB-positive and TB-negative patient sera, (a) NormPC, (b) PChemsPC, (c) OChemsPC, (d) PChcPC, and (e) DChemsPC; values represent the mean percentage gradient difference between TB-positive and TB-negative sera error bars represent the standard deviations, n=3.

Both FIGS. 3 and 4 were obtained using PChcPC SML as antigen-presenting liposomes. FIG. 3 confirmed the presence of anti-mycolic acid antibodies in the TB-positive patient serum sample ASPA019. The TB-negative status of patient sera ASPA004 is confirmed in FIG. 6 due to the equivalent gradient during initial binding of the inhibition step. PChcPC, like the other SMLs used here, contains a cholesterol moiety covalently built into an acyl chain of the phospholipid. The results suggest that this cholesterol moiety is not recognized by the ubiquitously present MA cross-reactive anti-cholesterol antibodies in human sera (Horvath & Biró, 2003). This maintained the signal difference between TB-positive and TB-negative patient sera by virtue of the specific anti-MA antibody activity present in TB-positive patient sera. The experiments were repeated for each of the remaining SML compounds, using the same TB-positive and TB-negative sera. A summary of the data is shown in FIG. 5 for all four SMLs. The Y-axis is defined as the mean percentage difference in inhibition of anti-MA antibody activity in TB-positive and TB-negative patient sera. This represents the resolution obtained by the MARTI-test to distinguish between a TB-positive and a TB-negative patient serum, using the four different SMLs, compared to normal PC as MA antigen carrier. The gradient was calculated for both channels within a window of 55 seconds during the initial binding portion of the inhibition step (about 3650 s to 3705 s). Channel 1's gradient was subtracted from channel 2. This was calculated for each replicate and the mean of the three values taken. The mean values for each TB-positive and negative sample were then subtracted from one another to obtain the mean percentage gradient difference between TB+ and TB− sera according to the following formula:

$$\% \ G_{1,2} = 100(\text{mean Gradient Ch 2} - \text{mean Gradient Ch 1})/\text{mean Gradient Ch 1} \ \% \ \text{GradDif} = \% \ G_{TB+ve} - \% \ G_{TB-ve}$$

The results indicate that the standard method using NormPC liposomes has the ability to differentiate between TB-positive and TB-negative patient sera with an approximately 20% difference by antibody binding inhibition activity. This contrasts to the same procedure performed with PChemsPC liposomes, with which no difference could be obtained between TB-positive and TB-negative patient sera (P<0.05), This was most probably due to the recognition of the cholesterol moiety of the PChemsPC by the universally prevalent anti-cholesterol antibodies in human sera (Horváth and Biró, 2003). OChemsPC and DChemsPC did show a tendency for their ability to distinguish the positive from the negative patient sera weaker than normal PC, but not at a level that inspires confidence in their use as liposome stabilizers for the MARTI-test. PChcPC displayed the most promising results by allowing the distinction between TB-positive and negative patient sera at least as strong as NormPC, but with the added quality of liposome stabilization as will be discussed in paragraph 3.3.2 below.

PChemsPC-MA, in contrast to PChcPC, displayed no specificity in its ability to detect TB biomarker anti-mycolic acid antibodies. This may be due to its propensity to form lipid raft-like structures in the liposomes (Brown & London, 2000), similar to what would happen if cholesterol was added to the PC liposomes at high concentration (Benadie et al., 2008). These raft-like structures, while stabilising the liposome, could be antigenic to anti-cholesterol antibodies that are universally present in all humans (Swartz et al., 1988, Biro et al., 2007). While PChemsPC-MA may present its MA and covalent cholesterol moiety as a cross-reactive antigen to anti-cholesterol antibodies, PChcPC-MA clearly does not do this, while OChemsPC-MA and DChemsPC-MA do this to a lesser extent. The number of abortive runs during MARTI decreased when using the SML compounds compared to NormPC, indicative of the higher liposome stability gained by the SMLs. This did not manifest in reduced standard deviations between identical SML test runs, compared to that of NormPC test runs in FIG. 5 as may have been anticipated. The size of the standard deviations in SPR-MARTI is therefore a function of elements such as equipment and handling, but not lack of stability of the liposome carriers of MA antigen.

Additional experimentation was performed to confirm the benefit of using the compound PChcPC. FIG. 6 depicts the % gradient difference between TB positive patients (ASPA 019 and BM-12) and TB negative patients (ASPA 004 and JS-09) sera. The greater sample number allowed for a statistically significant difference between the two at a 95% confidence interval.

Size Properties of Liposomes Effected by Sterol-Modified Lipids

The ability of the new SML liposomes to differentiate between TB-positive and TB-negative sera was compared to their physical properties. Any correlation may have the potential to provide insight into the mechanism whereby the SMLs achieve their unique liposomal antigenic presentation of MA and cholesterol in a real-world diagnostic application. All five liposome compositions were tested for size and zeta potential using the method listed in paragraph 3.2.

A standard method of representing liposome size data from a Zetasizer is a semi-logarithmic plot of size against light intensity (see FIG. 7). Display of the data for each liposome sample during a measurement event entails the determination of an averaged maximum of three Gaussian distribution plots (FIG. 7). There are a total of 10 different liposome samples, i.e. NormPC, PChemsPC, OChemsPC, PChcPC, and DChemsPC each with and without Mycolic acids. Earlier observations made when working with NormPC liposomes for the MARTI assay indicated a time-dependent decrease in repeatability of replicate experiments that became evident by eight hours after liposome formation. This was assumed to be due to a loss of liposome stability. Additional experimentation was performed to investigate the effect Mycolic acids have on liposome size.

FIG. 8 describes the effect inclusion of Mycolic acids has on liposome size with NormPC and PChcPC. This reduction in size may be a reason why the MARTI serum sample analyses proved accurate even after inclusion of a cholesterol moiety.

PChcPC-MA was the only SML liposome that appeared much smaller (20 nm on average) than its empty counterpart, similar to what was observed with NormPC. This correlates with its ability to present MA as a TB distinguishing antigen in the MARTI-test, compared to what was found with NormPC. In FIG. 5 PChcPC was the only compound that could provide a TB differentiating signal as good as, or better than NormPC.

To conclude, a SML (PChcPC) liposome was found that could present MA antigen in a way that could distinguish TB from among patient serum samples in MARTI, while stabilizing the liposomes. This was in support of the hypothesis stated initially. Another SML liposome (PChemsPC) was neither able to present MA functionally, nor to shrink in size when loaded with MA in the way that either NormPC-MA or PChcPC-MA could. The ability to present MA functionally therefore correlated to a shrink in liposome size when loaded with MA. Whether this physical dynamic liposome property represents a mechanism for functional antigenic presentation of MA remains to be determined, but is not contradicted by the results from two other SMLs that displayed reduced ability to both functionally present MA, and to shrink in size when loaded with MA antigen.

The Effect of SMLs on HLB and Size

As set out above cholesterol stabilises liposomes by reducing the crystal packing parameter and membrane fluidity. Cholesterol also reduces the hydrophile lipophile balance (HLB) that is involved in membrane curvature. A reduced HLB will result in membranes with less curved surfaces, i.e. larger sizes. The four sterol-modified phosphatidylcholines tested here were found to assemble into larger liposomes at around 30% concentration than could be achieved with normal phospatidylcholine alone (FIG. 8). This probably occurred to accommodate the cholesterol motif of the SMLs upon the formation of the liposomes. After the addition of MA, NormPC and PChcPC liposomes were smaller than their empty counterparts, which may imply a reduced cholesteroid antigenic clustering of MA and cholesterol motif brought about by increased curvature of the liposome surface and resulting in a better specificity of recognition by biomarker anti-MA antibodies in TB patient sera. Counter-intuitive to this is the expected decrease in hydrophile lipophile balance (HLB), when the hugely hydrophobic MAs are added to liposomes that should result in decreased membrane curvature and increased size. The data shows that when MA is added the expected pattern is seen with PChemsPC, but the opposite effect is observed with NormPC and PChcPC—liposome size is reduced. It is clear that much remains to be learned from the peculiar interaction between MA and different types of sterol-modified lipids. For now, it is sufficient to conclude that the particular problem of liposome stabilization in the MARTI test for TB diagnosis could be overcome with the application of SMLs. SMLs are revealed here as interesting and powerful tools to elucidate the antigenic nature of MAs for their optimal presentation as antigens to detect biomarker antibodies for tuberculosis.

The Effects of SMLs on Zeta Potential

Another indication of liposome stability can be observed through changes in zeta potential over time. The measurement of phospholipids provides negative zeta potential values due to the negative charge on the phosphate group (Van der Mei et al., 1988). The more negative the value the greater the zeta potential and therefore its stability (Li & Tian, 2002). This occurs by charge repulsion between liposomes (Akashi et al., 1998) resulting in reduced fusion among them. Liposomes are then maintained at a smaller size range, that here correlates with better specific antigenicity of MA to detect biomarker antibodies in TB patients (FIGS. 5 and 7).

Investigating the four different SMLs for their ability to induce liposomes that may act as more stable and functional MA antigen presenters in the MARTI-test, measurements were made one hour after initial liposome formation and thereafter at 24 and 120 hours. Three important and interesting liposome combinations were, PChcPC, PChemsPC and NormPC, representing the successful, impaired and reference MA antigen presentation systems respectively.

The data in FIG. 9 suggests an average negative numerical increase in zeta potential over time for all compounds lacking MA. The addition of mycolic acids gave rise to higher (more negative) zeta potential values in all cases one hour after formation. This is likely to occur due to the mycolic motif presenting its hydroxyl and carboxyl groups on the liposome surface. As time lapses, the zeta potential becomes more negative in all unloaded liposome types, but tends not to even out towards 120 hours in the case of PChemsPC. NormPC displays the greatest difference in zeta potential after 24 hours and rapidly equalises towards 120 hours. The determining factor for functional MA antigen presentation appears to be the rate at which the MA loaded liposome types increase their zeta potential to more negative values within 120 hours, Here PChcPC-MA achieves the highest zeta potential (−11.5 mV), compared to NormPC-MA (−9.0 mV) and PChemsPC (−8.0 mV). Critical in the case of PChemsPC-MA is that it changed direction from 24 hours towards less negative zeta potential, indicative of its unique behaviour that may relate to its inability to present MA as a functional antigen.

As with the liposome size property, it cannot be said at this stage why PChcPC-MA is such a good compound for functional MA antigen presentation. However, it physically relates to a decreased size and improved zeta potential after MA loading, which may provide a lead towards understanding PChcPC as an effective liposome stabilizer and MA antigen presenter in MARTI.

Conclusion

The challenges in TB diagnostics described above hindered the control of TB in the world. The WHO TB reports indicate that innovation in diagnostics is the best path to alleviating the problems confronting the management of the TB epidemic (Dacombe et al., 2009). SMLs were used in an attempt to stabilise surface-bound liposomes, extend their shelf-life, and provide a better inhibition signal for TB diagnosis. Biological investigation of antibody interactions to determine the TB status of a patient according to literature (Thanyani et al., 2008) was the defining parameter. Three physical properties are attributed to liposome stability, namely size (Winterhalter & Lasic, 1993), zeta potential (Li & Tian, 2002) and the addition of cholesterol (Connor et al., 1984, Brown & London, 2000, Lodish et al., 2004, Huang & Szoka 2008). The Applicant's data confirm the importance of these physical properties of liposomes when distinguishing between TB-positive and TB-negative patient sera. PChcPC was found to be best, followed by NormPC, while PChemsPC did distinguish between TB positive and TB negative patient sera. The applicant has found that a decrease in liposome size upon the addition of MA related to an ability to functionally present MA as an antigen for serum biomarker anti-MA antibody detection in determining the TB status of patients. A sustained numerical increase in negative zeta potential over time, a decrease in liposome size upon addition of MA and lipid bilayer rigidity provided by the cholesterol motif in the SML proved to be important. More intellectual investment in these concepts may validate this model. These results demonstrate the potential of inclusion of particular SMLs into liposomes to improve stability and capacity for MA antigen presenting, leading to increased sensitivity, specificity and reproducibility of liposomal diagnostic biosensor systems to detect anti-lipid antibodies as disease biomarkers in at least TB, but possibly also other diseases where anti-lipid biomarker antigen antibodies can be used as diagnostic parameter.

REFERENCES

Akashi, K, Miyata, H., Itoh, H., Kinosita, K., 1998. Formation of giant liposomes promoted by divalent cations: critical role of electrostatic repulsion. Biophysical Journal 74, 2973-2982.

Andersen, P., Munk, M. E., Pollock, J. M., Doherty, T. M., 2000. Specific immune-based diagnosis of tuberculosis. The Lancet 356, 1099-1104.

Benadie, Y., Deysel, M., Siko, D. G. R., Roberts, V. V., Van Wyngaardt, S., Thanyani, S. T., Sekanka, G., Ten Bokum, A. M. C., Collett, L. A., Grooten, J., Baird, M. S., Verschoor, J. A., 2008. Cholesteroid nature of free mycolic acids from M. tuberculosis. Chemistry and Physics of Lipids 152, 95-103.

Berggren, C., Johansson, G., 1997. Capacitance Measurements of Antibody-Antigen Interactions in a Flow System. Analytical Chemistry 69, 3651-3657.

Biro, A., Cervenak, L., Balogh A., Lörincz, A. Uray, K., Horváth, A., Romics I., Matkó J., Füst G., and László G. 2007. Novel anti-cholesterol monoclonal immunoglobulin G antibodies as probes and potential modulators of membrane raft-dependent immune functions. Journal of Lipid Research, 48, 19-29.

Brown, D. A., London, E., 2000. Structure and function of sphingolipid- and cholesterol-rich membrane rafts. Journal of Biological Chemistry 275, 17221-17224.

Connor, J., Yatvin, M. B., Huang, L., 1984. pH-sensitive liposomes: acid-induced liposome fusion. Proceedings of the National Academy of Sciences 81, 1715-1718.

Dacombe R., Murdoch, T., Guillerm, M. 2009, WHO Pathways to better diagnostics for Tuberculosis: A blueprint for the development of TB diagnostics. http://www.stoptb.org/resource_center/assets/documents/BluePrintT-B_annex_web.pdf Access date: 2010 Mar. 18.

Dotan, N., Altstock, R. T., Schwarz, M., Dukler, A., 2006. Anti-glycan antibodies as biomarkers for diagnosis and prognosis. Lupus 15, 442-450.

Engvall, E., Perlmann, P., 1971. Enzyme-linked immunosorbent assay (ELISA). Quantitative assay of immunoglobulin G. Immunochemistry 8, 871-874.

Floyd, K., Baddeley, A., Monica Dias, H., Falzon, D., Fitzpatrick, C., Gilpin, C., Glaziou, P., Hiatt, T., Pantoja, A., Sculier, D., Sismanidis, C., Timimi, H., Uplekar M., van Gemert W., 2011 WHO Global Tuberculosis Control Report, WHO Library http://www.who.int/entity/tb/publications/global_report/2011/gtbr11_full.pdf Access date: 2011 Oct. 24.

Gandhi, N. R., Moll, A., Sturm, A. W., Pawinski, R., Govender, T., Lalloo, U., Zeller, K., Andrews, J., Friedland, G., 2006. Extensively drug-resistant tuberculosis as a cause of death in patients co-infected with tuberculosis and HIV in a rural area of South Africa. The Lancet 368, 1575-1580.

Grohmann, F. L., Csempesz, F., Szogyi, M., 1998. Stabilization of small unilamellar dimyristoyl-phosphatidylcholine-liposomes by uncharged polymers. Colloid & Polymer Science 276, 66-71.

He, F., Zhang, L., Zhao, J., Hu, B., Lei, J., 2002. A thickness shear mode immunosensor for detection of M. tuberculosis with a new membrane material. Sensors and Actuators B: Chemical 85, 284-290.

He, Q.-Y., Lau, G. K. K., Zhou, Y., Yuen, S.-T., Lin, M. C., Kung, H.-F., Chiu, J.-F., 2003b. Serum biomarkers of hepatitis B virus infected liver inflammation: A proteomic study. Proteomics 3, 666-674.

Horváth, A., Biró, A., 2003. Anti-cholesterol antibodies in human sera. Autoimmunity Reviews 2, 272-277.

Huang, Z., Szoka, F. C., 2008. Sterol-modified phospholipids: cholesterol and phospholipid chimeras with improved biomembrane properties. Journal of the American Chemical Society 130, 15702-15712.

Kaufman, L., Ross, M. J., 2010. Biomarkers of HIV, Biomarkers. John Wiley & Sons, Inc., 381-400.

Lemmer, Y., Thanyani, S. T., Vrey, P. J., Driver, C. H. S., Venter, L., van Wyngaardt, S. ten Bokum, A. M. C., Ozoemena, K. I., Pilcher, L. A., Fernig, D. G., Stoltz, A. C., Swai, H. S. and Verschoor J. A. 2009. Detection of anti-mycolic acid antibodies by liposomal biosensors. Methods in Enzymology, 464, 79-92.

Lescuyer, P., Hochstrasser, D., Rabilloud, T., 2007. How shall we use the proteomics toolbox for biomarker discovery? Journal of Proteome Research 6, 28, 3371-3376.

Li, L. C., Tian, Y., 2002. Zeta Potential. Encyclopedia of Pharmaceutical Technology, 3020-3032.

Liang, M., Klakamp, S. L., Funelas, C., Lu, H., Lam, B., Herl, C., Umble, A., Drake, A. W., Pak, M., Ageyeva, N., Pasumarthi, R., Roskos, L. K., 2007. Detection of high- and low-affinity antibodies against a human monoclonal antibody using various technology platforms. ASSAY and Drug Development Technologies 5, 655-662

Liu, C.-C., Manzi, S., Ahearn, J. M., 2005. Biomarkers for systemic lupus erythematosus: a review and perspective. Current Opinion in Rheumatology 17, 543-549.

Lodish, H. F., Berk, A., Matsudaira, P., Kaiser, C. A., 2004. Molecular Cell Biology 5th Edition, W.H. Freeman and Company (USA).

Mire-Sluis, A. R., Barrett, Y. C., Devanarayan, V., Koren, E., Liu, H., Maia, M., Parish, T., Scott, G., Shankar, G., Shores, E., Swanson, S. J., Taniguchi, G., Wierda, D., Zuckerman, L. A., 2004. Recommendations for the design and optimization of immunoassays used in the detection of host antibodies against biotechnology products. Journal of Immunological Methods 289, 1-16.

Nicol, M. P., Workman, L., Isaacs, W., Munro, J., Black, F., Eley, B., Boehme, C. C., Zemanay, W., Zar, H. J., 2011. Accuracy of the Xpert MTB/RIF test for the diagnosis of pulmonary tuberculosis in children admitted to hospital in Cape Town, South Africa: a descriptive study. The Lancet Infectious Diseases 11, 819-824.

Okochi, K., Inaba, S. Tokunaga, K., Yoshizawa, H., Moori, H., Mizui, M., Ito, S., Yokoishi, F. Tsubaki, K., Yamano, H., Konishi, K., Kanemitsu, K., Shimizu, M., Watanabe, J., Nojiri, N., Nishioka, K., Tanaka, T., Kikuchi, S., Endo N., 1991. Effect of screening for hepatitis C virus antibody and hepatitis B virus core antibody on incidence of post-transfusion hepatitis. The Lancet 338, 8774, 1040-1041.

Ozoemena, K., Mathebula, N. S., Jeseelan, P., Toschi, G., Verschoor, J. A., 2010.

Rao, D. T., 2007. Diagnosis of Tuberculosis. http://www.slideshare.net/doctorrao/diagnosis-of-tuberculosis-drt-vrao. Access date 2011 Oct. 16.

Sattler, K. D., 2010. Handbook of Nanomedicine and Nanorobotics, Volume 7, CRC Press (USA).

Soleh, V., 2011. FIND negotiated prices for Xpert® MTB/RIF and country list. http://www.finddiagnostics.org/

Sekanka, G., Baird, M., Minnikin, D., Grooten, J., 2007. Mycolic acids for the control of tuberculosis. Expert Opinion on Therapeutic Patents 17, 315-331.

Steingart, K. R., Flores, L. L., Dendukuri, N., Schiller, I., Laal, S., Ramsay, A., Hopewell, P. C., Pai, M., 2011. Commercial serological tests for the diagnosis of active pulmonary and extrapulmonary tuberculosis: an updated systematic review and meta-analysis. PLoS Medicine 8, 8, 1-19.

Swartz, G. M., Gentry, M. K., Amende, L. M., Blanchette-Mackie, E. J., Alving, C. R., 1988. Antibodies to cholesterol. Proceedings of the National Academy of Sciences 85, 1902-1906.

Thanyani, S. T., Roberts, V., Siko, D. G. R., Vrey, P., Verschoor, J. A., 2008. A novel application of affinity biosensor technology to detect antibodies to mycolic acid in tuberculosis patients. Journal of Immunological Methods 332, 61-72.

Thomas, G., Sundaram, L., 2010. WHO endorses new rapid tuberculosis test. http://www.who.int/tb/features_archive/new_rapid_test/en/Access date 2011 Nov. 18.

Verschoor J. A., Siko, D. G. R., Van Wyngaardt, S., 2005. Method for detecting mycobacterial infection, U.S. Pat. No. 7,851,166 B2.

Van der Mei, H. C., Léonard, A. J., Weerkamp, A. H., Rouxhet, P. G., Busscher, H. J., 1988. Surface properties of *Streptococcus salivarius* HB and nonfibrillar mutants: measurement of zeta potential and elemental composition with X-ray photoelectron spectroscopy. Journal of Bacteriology 170, 2462-2466.

Vereschoor J. A., Siko, D. G. R., Van Wyngaardt, S., 2005. Method for detecting mycobacterial infection, U.S. Pat. No. 7,851,166 B2.

Van Deun, A., Martin, A., Palomino, J. C., 2010. Diagnosis of drug-resistant tuberculosis: reliability and rapidity of detection (In: State of the Art series vol 3. Drug-resistant Tuberculosis. Ed. Chiang). The International Journal of Tuberculosis and Lung Disease 14, 131-140.

Uhlenbeck, G. E., Ornstein, L. S., 1930. On the Theory of the Brownian motion. Physical Review 36, 823.

Vassall, A., van Kampen, S., Sohn, H., Michael, J. S., John, K. R., den Boon, S., Davis, J. L., Whitelaw, A., Nicol, M. P., Gler, M. T., Khaliqov, A., Zamudio, C., Perkins, M. D., Boehme, C. C., Cobelens, F., 2011. Rapid diagnosis of Tuberculosis with the Xpert MTB/RIF assay in high burden countries: a cost-effectiveness analysis. PLoS Medicine 8, 11, 1-14.

Wilson, D., 2005. Diagnosing HIV-associated tuberculosis. Southern African Journal of HIV Medicine 6, 23-26.

Winterhalter, M., Lasic, D. D., 1993. Liposome stability and formation: experimental parameters and theories on the size distribution. Chemistry and Physics of Lipids 64, 35-43.

Zhou, L., He, X., He, D., Wang, K., Qin, D., 2011. Biosensing technologies for *Mycobacterium tuberculosis* detection: status and new developments. Clinical and Developmental Immunology. 2011, 1-8.

What is claimed is:

1. A lipid antigen-presenting liposomal composition for the detection of lipid antigen specific biomarker antibodies in antibody containing biological samples, the composition comprising
phosphatidylcholine liposomes comprising 1-palmitoyl-2-cholesterylcarbonoyl-sn-glycero-3-phosphocholine and mycolic acid,
the liposomes having a diameter that is at least 20 nm smaller and a curvature that is at least 20% greater than that of liposomes that are the same except that they lack mycolic acid,
and a zeta potential that is more negative, for up to 120 hours after formation, than the zeta potential of liposomes that are the same except that they lack 1 palmitoyl-2-cholesterylcarbonoyl-sn-glycero-3-phosphocholin;
wherein the liposomes functionally present mycolic acid as an antigen, and
wherein the liposomes do not react with anti-cholesterol antibodies.

2. The composition as claimed in claim 1, which comprises 20-50 mol percent of the 1-palmitoyl-2-cholesterylcarbonoyl-sn-glycero-3-phosphocholine and the mycolic acid and 45-80 mol percent of the phosphatidylcholine.

3. The composition as claimed in claim 2, which comprises 30 mol percent of the 1-palmitoyl-2-cholesterylcarbonoyl-sn-glycero-3-phosphocholine, 10 mol percent of the mycolic acid and 60 mol percent of the phosphatidylcholine.

4. The composition as claimed in claim 1, in which the mycolic acid is derived from mycobacteria selected from the group consisting of virulent and pathogenic mycobacteria.

5. The composition as claimed in claim 1, in which the mycolic acid is derived from *Mycobacterium tuberculosis*.

6. The composition as claimed in claim 1, in which the mycolic acid is in a form selected from the group consisting of homogenous and heterogeneous compound mixtures.

7. A method of preparing a lipid antigen-presenting liposomal composition for the detection of lipid antigen specific biomarker antibodies in antibody containing biological samples, the method including the step of combining 1-palmitoyl-2-cholesterylcarbonoyl-sn-glycero-3-phosphocholine, phosphatidylcholine and mycolic acid to produce liposomes that comprise 1-palmitoyl-2-cholesterylcarbonoyl-sn-glycero-3-phosphocholine, phosphatidylcholine and mycolic acid and that have mycolic acid antigen integrated into the liposome layer, wherein the liposomes stably decrease in diameter by at least 20 nm and increase in curvature by at least 20% with introduction of mycolic acid in order to functionally present mycolic acid antigens due to reduced antigen clustering, and wherein the zeta potential of the liposomes is more negative than the zeta potential of liposomes that do not contain 1-palmitoyl-2-cholesterylcarbonoyl-sn-glycero-3-phosphocholine for up to 120 hours after formation.

8. A method of detecting antigen specific biomarker antibodies for the diagnosis of active tuberculosis, the method including the steps of:
providing a lipid antigen-presenting liposomal composition comprising liposomes comprising 1-palmitoyl-2-cholesterylcarbonoyl-sn-glycero-3-phosphocholine, phosphatidylcholine and mycolic acid as claimed in claim 1;
immobilizing the liposomes to produce immobilized mycolic acid antigens comprising the mycolic acid;
obtaining a first, a second and a third sample from a human or animal suspected of having active tuberculosis, wherein each sample may contain antibodies to the antigen, the first sample having a lower concentration by dilution than the second and third samples;
exposing part of the first sample to the immobilized mycolic acid antigens in a test vessel;
exposing part of the first sample to the immobilized mycolic acid antigens in a control vessel;

exposing the second sample to the lipid antigen-presenting liposomal composition provided in the first step;
exposing the third sample to liposomes not containing mycolic acid antigen;
adding the second sample, after exposure to the mycolic acid antigen-containing liposomal composition provided in the first step, to the test vessel;
adding the third sample, after exposure to the liposomes not containing mycolic acid, to the control vessel;

detecting binding of antibodies to the mycolic acid antigen in both the test and control vessels in real time; and comparing the degree or extent of binding between the test and the control vessels, the weaker binding in the test vessel being an indicator of the presence of antibodies to the mycolic acid antigen in the sample that indicates active tuberculosis in the human or animal from which the sample originated.

9. The method as claimed in claim 8, in which immobilizing the liposomes to produce immobilized mycolic acid antigens comprising the mycolic acid is carried out on an activated surface.

10. The method as claimed in claim 9, in which the activated surface is a hydrophobic biosensor cuvette surface.

11. The method as claimed in claim 9 which uses a surface plasmon resonance biosensor.

12. The method as claimed in claim 9 which is carried out using the modified mycolic acid antibodies real-time inhibition (MARTI) procedure.

13. The method as claimed in claim 7, in which the lipid antigen-presenting liposomal composition comprises 20-50 mol percent of the 1-palmitoyl-2-cholesterylcarbonoyl-sn-glycero-3-phosphocholine and mycolic acid and 45-80 mol percent of the phosphatidylcholine.

* * * * *